(12) United States Patent
Gobius Du Sart et al.

(10) Patent No.: US 10,466,169 B2
(45) Date of Patent: Nov. 5, 2019

(54) QUANTIFICATION METHOD OF MESO-LACTIDE IN A LACTIDE-CONTAINING COMPOSITION

(71) Applicant: PURAC BIOCHEM BV, Gorinchem (NL)

(72) Inventors: Gerrit Gobius Du Sart, Gorinchem (NL); Johannes Adrianus Kamp, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 0 days.

(21) Appl. No.: 15/751,132

(22) PCT Filed: Jul. 28, 2016

(86) PCT No.: PCT/EP2016/067993
§ 371 (c)(1),
(2) Date: Feb. 7, 2018

(87) PCT Pub. No.: WO2017/025338
PCT Pub. Date: Feb. 16, 2017

(65) Prior Publication Data
US 2018/0238795 A1    Aug. 23, 2018

(30) Foreign Application Priority Data

Aug. 10, 2015 (EP) ..................................... 15180395

(51) Int. Cl.
*G01N 21/35* (2014.01)
*G01N 21/359* (2014.01)
*C07C 59/08* (2006.01)

(52) U.S. Cl.
CPC ........... *G01N 21/359* (2013.01); *G01N 21/35* (2013.01); *C07C 59/08* (2013.01)

(58) Field of Classification Search
CPC ....... G01N 21/359; G01N 21/35; C07C 59/08
See application file for complete search history.

(56) References Cited

U.S. PATENT DOCUMENTS 6,114,495 A * 9/2000 Kolstad .................. C08G 63/90
                                                                525/413
6,162,644 A   12/2000 Choi et al.
(Continued)

FOREIGN PATENT DOCUMENTS

| JP | 2015-518970 A | 7/2015 |
| WO | 2013/187758 A1 | 12/2013 |
| WO | 2015/086494 A1 | 6/2015 |

OTHER PUBLICATIONS

Braun et al., "Infrared Spectroscopic Determination of Lactide Concentration in Polylactide: An Improved Methodology," Macromolecules, 2006, vol. 39, pp. 9302-9310.
(Continued)

*Primary Examiner* — Hugh Maupin
(74) *Attorney, Agent, or Firm* — Oliff PLC

(57) ABSTRACT

A method for quantification of the amount of meso-lactide in a composition containing at least one other lactide stereoisomer with respect to the total amount of lactide stereoisomers in the composition. The quantification is based on measurements performed on absorptions in the Infra-Red region of the electromagnetic spectrum. Small amounts of meso-lactide in a lactide composition could be measured online in an easy and reproducible manner. Preferably near-IR has been used in this quantification method. The method can be applied with great advance in a lactide production device.

14 Claims, 3 Drawing Sheets

(56) References Cited

U.S. PATENT DOCUMENTS

Figure 1:
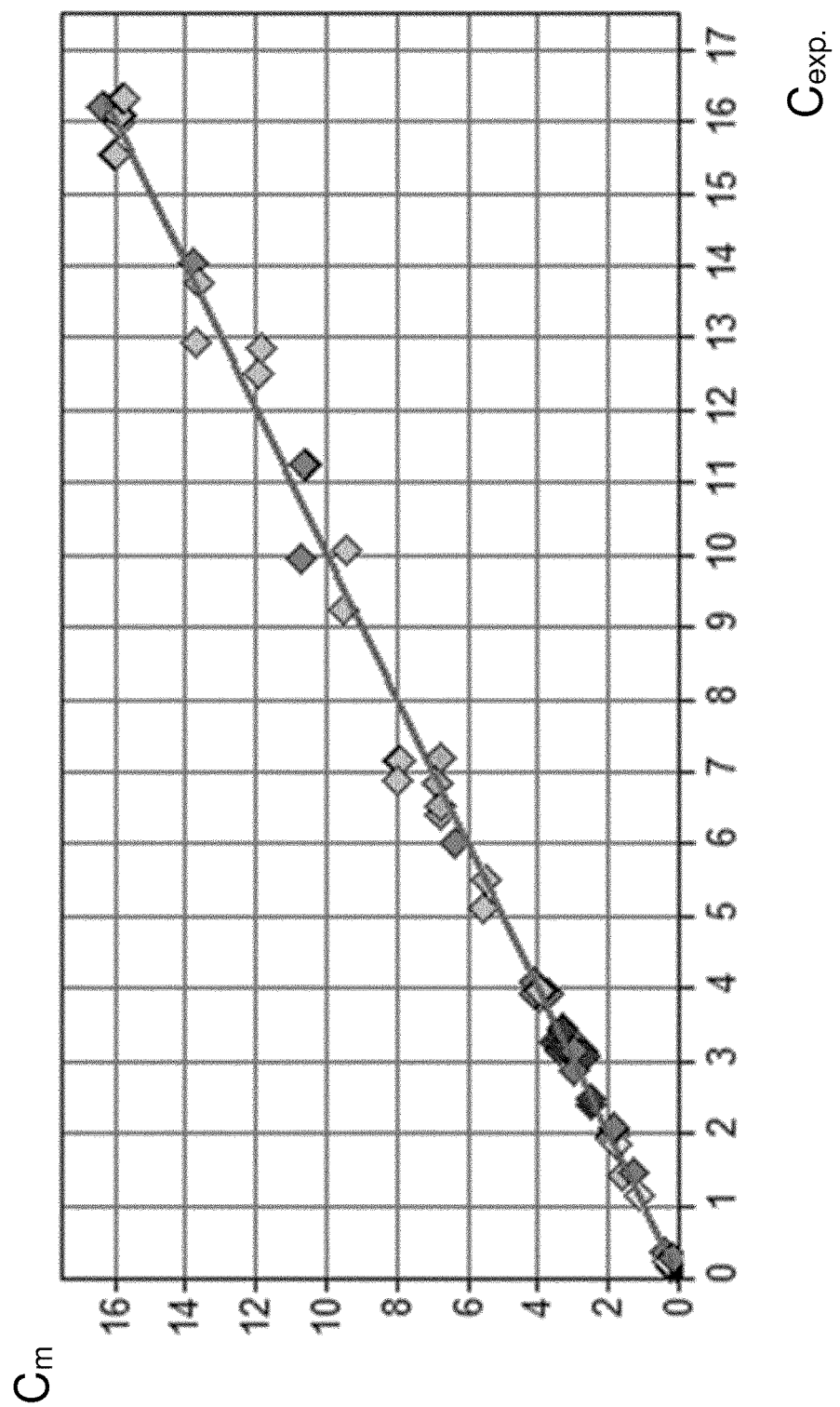

2005/0222379 A1 10/2005 Matsuo et al.
2015/0168295 A1* 6/2015 Gobius Du Sart .. G01N 21/359
250/339.07

OTHER PUBLICATIONS

Gonçalves et al., "Optical Properties," Chapter 8, Poly(lactic acid): Synthesis, Structures, Properties, Processing, and Applications, 2010, pp. 97-112.
Thosar et al., "Determination of copolymer ratios of poly(lactide-co-glycolide) using near-infrared spectroscopy," Journal of Pharmaceutical and Biomedical Analysis, 1999, vol. 20, pp. 107-114.
Nov. 7, 2016 International Search Report issued in International Patent Application No. PCT/EP2016/067993.
Nov. 7, 2016 Written Opinion of the International Searching Authority issued in International Patent Application No. PCT/EP2016/067993.
Apr. 18, 2019 Translation of Office Action issued in Japanese Patent Application No. 2018-506313.
Wu et al., "Density functional theory study on lactides: Geometries, IR, NMR and electronic spectra," Journal of Molecular Structure: THEOCHEM, vol. 816, No. 1-3, Jul. 24, 2007, pp. 13-19.
Mar. 29, 2019 Office Action issued in European Patent Application No. 16750675.7.

* cited by examiner

QUANTIFICATION METHOD OF MESO-LACTIDE IN A LACTIDE-CONTAINING COMPOSITION

FIELD OF THE INVENTION

The present invention relates to a method for quantification of the amount of meso-lactide in a composition containing at least one other lactide stereoisomer with respect to the total amount of lactide stereoisomers in the composition.

BACKGROUND OF THE INVENTION

Lactide is a well-known intermediate product which can be used in the manufacturing of polymer materials, like polylactic acid (PLA) or PLA-containing copolymers. Lactide (sometimes called dilactide) is a cyclic dimer of lactic acid and is usually manufactured by means of a two-step process. In the first step of this process, lactic acid is polymerized by means of polycondensation into a so-called pre-polymer or oligomer, having a relatively low molecular weight. In the second step, crude lactide is formed from this pre-polymer or oligomer material by means of a so-called 'backbiting' process in the presence of a suitable catalyst. The crude lactide material formed in this process can be purified, for example by means of (repeated) crystallization and/or (repeated) distillation. The so-obtained purified lactide may subsequently be used in a polymerization process for the manufacture of PLA or PLA-containing copolymers.

It is well-known that lactide can exist in three different stereochemical structures, which have a diastereomeric relationship. These different structures can be distinguished as R,R-lactide (or D-lactide), S,S-lactide (or L-lactide) and R,S-lactide (or meso-lactide). These three types of lactide are referred to as lactide stereoisomers. Furthermore, a stoichiometric mixture of D- and L-lactide is usually referred to as racemic lactide or rac-lactide. Within the scope of the present invention, the word 'lactide' (or dilactide) used in the absence of a prefix (meso-, L-, or D-) generally refers both to any of the three pure lactides (being composed of only one stereoisomer) as well as to mixtures of two or more of the pure lactides.

Knowledge of the purity of the produced lactide is important. This relates to impurities, like free acids (such as lactic acid and lactoyl lactic acid) or water, which impurities may have a strong influence on a lactide-to-PLA polymerization process. This also relates to the so-called stereochemical purity of the produced lactide material. The relative amount (s) of the before-mentioned lactide enantiomer(s) in a final polymer-grade lactide depends firstly on the stereochemical purity of the lactic acid used as starting material in the production of lactide. Secondly, undesired lactide enantiomer(s) can also be formed during the lactide production process itself as a result of racemization.

The amount of meso-lactide will increase if only one of the two stereo-centers in pure L-lactide or pure D-lactide racemases (epimerization). Finally, the details of the purification processes downstream of the production process will determine the stereochemical composition of the product stream(s).

Currently, chromatographic methods are still used in order to determine or quantify the amount of meso-lactide in a composition containing meso-lactide and at least one other lactide enantiomer with respect to the total amount of lactide enantiomers. In practice these methods require tedious sample preparation and work-up of lactide-containing material as well as chromatographic analysis in order to determine the exact amount of meso-lactide in the composition.

According to the experience of the inventors, the known chromatographic methods for quantification of meso-lactide in the total amount of lactide enantiomers are time-consuming and labor-intensive in their use. Moreover, the results of the known quantification methods are not immediately available.

Therefore, determination of meso-lactide by means of the known separation methods has the drawbacks of being less suitable to monitor the lactide quality online under mass production circumstances.

SUMMARY OF THE INVENTION

In Applicants view, there exists a strong need to simplify the known quantification methods of the amounts of meso-lactide in a material containing also one or more further lactide enantiomers. It is therefore an object of the present invention to provide an accurate yet simple, flexible and cost-effective method for the quantification of meso-lactide in a crude lactide mixture, which method does not require a time-consuming and complicated experimental handling. Such quantification method should preferably be operable in various stages of a lactide production process and should also be operable in the monitoring of the purity of lactide during its storage. Such quantification method should also be applicable for checking the stereochemical purity of meso-lactide.

To meet these and/or possible further objectives of the present invention, the invention pertains to a method for quantification of the amount of meso-lactide in a composition containing at least one other lactide stereoisomer with respect to the total amount of lactide stereoisomers in the composition, which method is further characterized in that absorptions in the Infra-Red region of the electromagnetic spectrum of the composition are determined, and the amount of meso-lactide is quantified with reference to a standard.

The invention is based on the experimentally obtained insight of the inventors that rather small amounts of meso-lactide can be measured and quantified in a lactide-containing material by means of Infra Red (IR) measurements. As the chemical structures of the various stereoisomers are quite similar, it was surprising that accurate and reliable determination of the amount of meso-lactide in a mixture with one or both of the other lactide isomers is possible at all.

By using this method, amounts of meso-lactide in a material with additional lactide enantiomer(s) down to 1% by weight (wt. %) or less can be measured and quantified in an accurate and reproducible manner.

It is noted that WO2013/187758 describes a method for the quantification of the amount of lactide in a lactide-based polymer matrix via infrared spectroscopy measurements. In the procedure of this document the total lactide content is determined in a polymeric matrix. This is different from, and not related to, the determination of meso-lactide in a mixture which further contains other lactide stereoisomers. The same applies to the publication of B. Braun et al., "Infrared spectroscopic determination of lactide concentration in polylactide: an improved methodology", Marcromolecules Vol. 39, no. 26, pp 9302-9310, and to the publication of C. B. M. Goncalves, "Optical Properties", Chapter 8 in "Poly (lactic acid): synthesis, structures, properties, processing, and applications, edited by R. Auras et al., John Wiley & Sons 2010.

The quantification method of the present invention requires determination of absorptions in the Infra-Red region of the electromagnetic spectrum of a sample, and quantifying the amount of meso-lactide with reference to a standard. The use of a standard is conventional in the art of quantification. It entails the preparation of compositions with known amounts of the compound to be determined, in the present case meso-lactide, and determining the spectrum obtained for these known compositions. As will be clear to the skilled person, the compositions used for setting the standard should of course be as close as possible in composition to the composition in which the meso-lactide is to be quantified, e.g., with reference to the amounts of L-lactide, D-lactide and/or optional further components. This will help to make the quantification method as accurate as possible.

The composition which can be subject to the present invention comprises meso-lactide and at least one other lactide stereoisomer. In one embodiment, the composition comprises at least 50 weight percent of the total of meso-lactide and other lactide stereoisomers, in particular at least 70 weight percent, in some embodiments at least 80 weight percent, or even at least 90 weight percent. In this embodiment, the composition may comprise up to 50 weight percent of lactic acid oligomers with a degree of polymerisation in the range of 3 to 10, in particular up to 30 weight percent, more in particular up to 20 weight percent, in some embodiments up to 10 weight percent. The composition can, for example, be the intermediate product in a lactide production process, as will be discussed in more detail below.

The competition will generally not comprise substantial amounts of polylactide, which is defined as lactide polymer with a degree of polymerisation of above 20. In the present invention, polylactide, if present, will generally be present in the composition in an amount of 10 weight percent or less, in particular in an amount of 5 weight percent or less, more in particular in an amount of 2 weight percent or less.

Compared with the known chromatographic methods, the data analysis with the invented method is far less time-consuming. Moreover, the invented method does not require additional sample preparation. Actually, the IR measurements can be performed online and in bulk. In practice, determining the amount of meso-lactide by means of HPLC and/or GC methods, including the typical precipative sample handling, takes at least several hours. This means that the known chromatographic methods have a relatively long throughput time, which is unacceptable for production control purposes.

It is noted that in current application, the IR region is defined to range from wavelengths approximately 0.8-25 µm or wave numbers of 14000-400 cm$^{-1}$. In this range, encompassing the mid- and near infrared regions, molecular vibrations and other molecular movements of organic molecules can be observed. It has surprisingly been found that the small structural differences between meso-lactide and the other two lactide stereoisomers give sufficient differences in the energies absorbed due to their internal molecular movements. As a result, the absorptions of meso-lactide on the one hand and the other two lactide stereoisomers on the other hand in the IR electromagnetic spectrum are sufficiently different in order to allow proper quantification of these individual stereoisomers in a mixture. Such mixture can comprises meso-lactide with only one or with both other stereoisomers.

In the mid-IR region it is well possible to assign specific absorptions to molecular functions. From an online monitoring perspective, it is however desired to use near-IR spectroscopy. The relevant absorption peaks to be measured are in the near-IR region rather broad and/or overlapping, resulting in complex near-IR spectra. In these spectra, the various peaks cannot unambiguously be assigned to specific vibrations. Nevertheless, both mid and near-IR measurements on samples containing mixtures of well-determined amounts of meso-lactide combined with one or both other lactide enantiomers surprisingly show that meso-lactide calibration curves can be determined with very good fits. It can therefore be concluded that very small amounts of meso-lactide in a material containing in addition a high amount of other enantiomer(s) can be quantified in a relatively simple manner by means of both techniques. As indicated above, the IR region is defined to range from wavelengths approximately 0.8-25 µm or wave numbers of 14000-400 cm−1. The near-IR region is defined to range from wave numbers of 14000-4000 cm−1. The mid-IR region is defined to range from 4000-400 cm−1. In the method according to the invention, it is possible to use the entire 14000-400 cm−1 region. It is, however, also possible to use part of the region, e.g., the mid-IR region, or part thereof, or the near-IR region, or part thereof. Within the near-IR region, the use of a spectrum obtained in the range of 6100 and 5100 cm−1 provide most relevant information (first overtones). Therefore, the use of a spectrum in this region may be particularly attractive. It is within the scope of the skilled person to define a suitable wave length range on the basis of the guidance give above.

A preferred embodiment of the method according to the present invention is characterized in that the amount of meso-lactide is measured at a temperature at which the lactide stereoisomers present in the composition are molten. In practice this means that the measurements should be performed at temperatures above 97° C. to have also the L- or D-lactide in liquid form. Pure meso-lactide melts at a temperature of about 55° C. It is preferred for the composition to be tested to be in the liquid form in its entirety.

It is stressed that the method of the present invention can in principle also be applied when using mixtures of lactide stereoisomers which are in solid form. However, samples of lactide stereoisomers in solid form may require additional sample preparation time. In addition, sample (in)homogeneity may make analysis of the measured data difficult. In practice this means that the measurements should be performed at temperatures above approximately 55° C. for measuring pure meso-lactide and preferably above approximately 97° C. for measuring the amount of meso-lactide as a minor side-product in L- or D-lactide as well as in mixtures of latter two lactides.

Another preferred embodiment of the invented method is the case where the amount of meso-lactide is below 25 wt. % of the total amount of lactide stereoisomers present in the composition, preferably below 10 wt. %. In practice, the amounts of meso-lactide obtained in the production of pure L- or D-lactide are far less than the amount of the pure L- or D-lactide component itself. In many situations, these amounts of meso-lactide are less than 25 wt. %, and often less than 10 wt. %. The presently invented method can be used with advantage to measure such relative amounts of meso-lactide in a mixture containing meso-lactide as a minor lactide component and predominantly L- or D-lactide, or a mixture of L- and D-lactide. The amount of meso-lactide in the composition tested in accordance with the present invention may be much lower than 25 wt. % or 10 wt. %, calculated on the total amount of lactide stereoisomers present in the composition, e.g., less that 5 wt. %, in particular less than 2 wt. %, or even less than 1 wt. %, in some embodiments less than 0.5 wt. %.

A further preferred embodiment of the method in accordance to the present invention has the feature that the amount of meso-lactide is measured in a lactide production process. During production of lactide using lactic acid as a starting product, it is important that the amount of the usually undesired lactide stereoisomer meso-lactide can be measured in crude and purified lactide streams. The presently invented quantification method is considered to be very suitable for this purpose. Therefore, in one embodiment, the present invention pertains to a process for producing lactide, which comprises the step of depolymerisation of lactic acid oligomers in a lactide reactor, wherein during the process one or more samples are taken, and the amount of meso-lactide in one or more samples is quantified with the method according to the invention. Methods for producing lactide comprising the step of depolymerisation of lactic acid oligomers are in themselves known in the art. In general, lactic acid oligomers of relatively low molecular weight (polymerization degree usually between 6 and 50) are heated in a so-called lactide reactor, usually in the presence of a suitable catalyst. Under proper reaction conditions, the lactic acid oligomers are depolymerized by a process known as 'back-biting', whereby the cyclic ester lactide is formed.

The catalyst which is generally used can be any catalyst which is suitable for promoting the depolymerisation of the oligomers to lactide. Suitable catalysts are generally metals or compounds of metals of groups IV, V and VIII of the Periodic Table. Preferred are metals of groups IV, notably Sn as the metal (powdered), oxide, halogenide or carboxylate, or V, notably Sb, usually as the oxide Sb2O3. Preferred herein are Sn(II)carboxylates, especially those that are soluble in the molten oligomer and exemplified by stannous bis(2-ethylhexanoate), commonly referred to as stannous octoate. The catalyst will be employed in catalytically-effective amounts which can readily be determined through trial runs. For example, with stannous octoate as the catalyst, the catalyst will generally be used in an amount of about 0.01 to about 5 wt. %, usually from about 0.3 to 3%. A suitable reaction temperature will generally be in the range of 150-300° C., in particular in the range of 180-220° C. The pressure may vary within broad ranges, e.g., between 1 mbar and 50 mbar, preferably between 2 and 10 mbar.

Also interesting is the embodiment of the invention which has the feature that the lactide production process is a continuous process. Although the invented method of quantification of meso-lactide can also be applied in a batch process, it is believed that its use in continuous processes provides most advantages. In such a continuous lactide production process, the measurement results are preferably available instantly. As a result of the present invention, the process and quality control of such a continuous process may become much simpler. Moreover, undesired deviations of the meso-lactide content obtained during the lactide production process can be now be determined at a very early stage, so that changes in process parameters to repair these deviations can be applied in an early stage. As a result, possible lactide quality problems as well as production losses can be minimized.

The lactide obtained by depolymerization of oligomers of lactic acid is called 'crude lactide', indicating that it may contain significant amounts of meso-lactide and/or impurities. It is therefore highly preferred when lactide removed from the lactide reactor is subsequently purified, preferably by distillation. Therefore, in one embodiment, the invention pertains to a process for producing lactide, which comprises the step of depolymerisation of lactic acid oligomers in a lactide reactor, and the step of subjecting the reaction product obtained by the depolymerisation reaction to a distillation step in which lactide is distilled from the reaction product, wherein during the process one or more samples are taken, and the amount of meso-lactide in one or more samples is quantified with the method according to the invention.

A further interesting embodiment of the presently invented quantification method is characterized in that the amount of meso-lactide in the continuous process is measured simultaneously at different stages of the lactide production process. This may enable a complete production control over the whole lactide production process, thereby resulting in a very efficient and cost-effective overall lactide manufacture. In case that there are more quantification points of interest in the production process, like in the crude liquid lactide and in (partly) purified liquid lactide, said quantification of meso-lactide can be performed by using multiple measuring probes in combination with a single IR measuring apparatus. The resulting data can be calculated instantaneously and preferably with a single data calculator. So, online monitoring of the change in the measured impurities in a continuous lactide production process, for example by incorporating the measurement in an automated control system, is now possible.

A very efficient and therefore preferred embodiment concerns the design of the process whereby the amount of meso-lactide is measured in a liquid lactide stream which is derived from the lactide reactor. The produced lactide may be removed from the lactide reactor as crude lactide in vapor form or in molten form. In case of lactide in vapor form, this lactide is preferably be liquefied by the use of one or more condensers. Another very efficient and therefore preferred embodiment concerns the design of the process whereby the amount of meso-lactide is measured in a liquid lactide stream which is derived from the distillation column. A further efficient and therefore preferred embodiment concerns the design of the process whereby the amount of meso-lactide is measured in a liquid lactide stream which is derived from a condenser onto which lactide has been condensed and subsequently remolten. The so-obtained lactide may be part of the lactide production process itself or of a lactide devolatilization process used in polylactide production. Especially in latter PLA production process, quality control of the withdrawn lactide is of great importance, especially in case that the so-obtained lactide needs to be directly or indirectly recycled to the lactide or PLA production process.

Very interesting is also the embodiment of the meso-lactide quantification method, which is characterized in that the quantification is based on measurements performed on absorptions in only the near Infra-Red region of the electromagnetic spectrum. Although measurements in the near-IR spectral range between 6100 and 5100 $cm^{-1}$ provide most relevant information (first overtones), measurements in a broader nIR range like between 12000 and 4000 $cm^{-1}$ are also well suitable. Also interesting is the embodiment of the invented method in which the results of the quantification of the amounts of meso-lactide with respect of the total amount of lactide enantiomers is used to control production parameters, in order to adjust production of lactide. Implementation of this embodiment may result in a drastic increase in the efficiency of the production of the lactide stereoisomer of the desired type or of the desired mixture of two or more lactide stereoisomers.

BRIEF DESCRIPTION OF THE INVENTION

Figure 2:
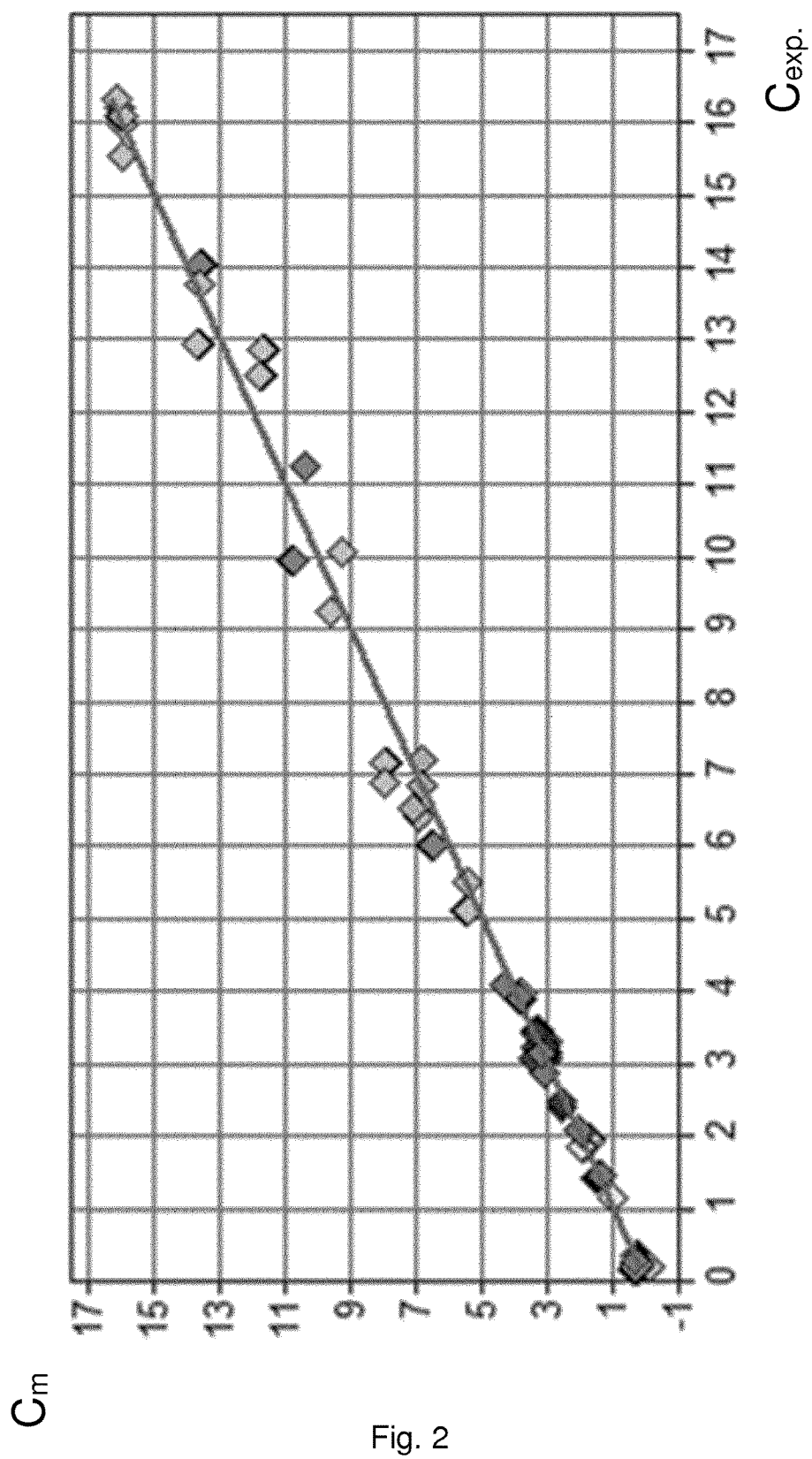
Figure 3:
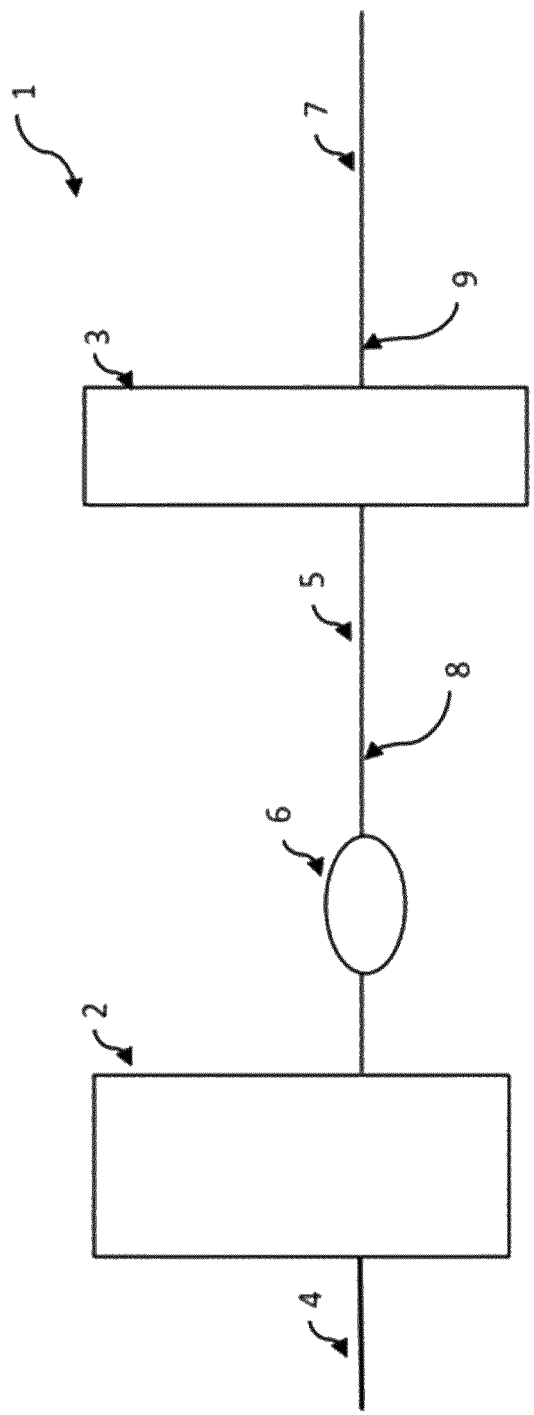

The present invention is described in more detail and elucidated by different examples and a drawing, in which FIG. 1 shows a near-IR cross validation plot of measured and calculated data of meso-lactide in L-lactide, FIG. 2 shows a mid-IR cross validation plot of measured and calculated data of meso-lactide in L-lactide, and FIG. 3 shows in schematic form a lactide production device in which the invented method can be implemented.

DETAILED DESCRIPTION OF THE INVENTION

In an experiment, approximately 600 grams of L-lactide (PURALACT B3, flakes (Corbion)) were melted under a nitrogen blanket in a round bottom flask with 5 necks by heating the flask in a heating bath. The temperature of the lactide inside the round bottom flask was controlled by a temperature gauge. Depending on the type of measurements, a near-IR probe or a mid-IR was inserted in the molten L-lactide and the data acquisition was started. Small amounts of meso-lactide (Corbion made) were added to the molten L-lactide. IR spectra (either near-IR or mid-IR) were recorded after each meso-lactide addition. For the near-IR measurements, a Bruker IR apparatus was used for the measurements, adapted with a nIR probe (Matrix F duplex). For the mid-IR measurements, a Bruker IR apparatus was used for the measurements, adapted with a mid-IR probe (Matrix MF duplex). After the measurements, samples were taken in order to determine the amount of meso-lactide in the lactide composition experimentally. These amounts were determined by means of HPLC and GC techniques, known as such in the art. These values were used to construct a model to predict meso-lactide contents online.

FIG. 1 shows a so-called cross-validation curve of amounts (in weight. %) of meso-lactide in L-lactide as measured by near-IR. In this Figure, the modeled amount ($C_m$) is plotted as a function of the experimentally determined concentration ($C_{exp}$). In order to obtain these data, small amounts of meso-lactide were added to the L-lactide and near-IR spectra measured from these mixtures. Based on the experimental results, the recorded spectra and the software used, the plotted best-fit curves could be obtained for both the calibration curve and the cross validation curve.

From FIG. 1, it can be concluded that with the used near-IR quantification method it is possible to determine amounts of meso-lactide in L-lactide within a range of 0, 1 to 16 weight. % with a confidence interval of 0.33 wt. % (RMSECV, root mean square error of cross-validation, for the whole model).

FIG. 2 shows a similar cross-validation curve of amounts (in weight. %) of meso-lactide in L-lactide as measured by mid-IR. In this Figure, the modeled amount ($C_m$) is plotted as a function of the experimentally determined concentration ($C_{exp}$). In order to obtain these data, small amounts of meso-lactide were added to the L-lactide and mid-IR spectra measured from these mixtures. Based on the experimental results, the recorded spectra and the software used, the plotted best-fit curves could be obtained for both the calibration curve and the cross validation curve.

From FIG. 2, it can be concluded that with the used mid-IR quantification method it is possible to determine amounts of meso-lactide in L-lactide within a range of 0, 1 to 16 weight. % with a confidence interval of 0.35 wt. % (RMSECV, root mean square error of cross-validation, for the whole model.

In practice, the near-IR probe appeared to be easier in practical use as compared with the mIR probe, as latter probe had to be cooled with nitrogen during the measurements.

In FIG. 3, a lactide production device 1 is shown in schematic drawing. This device contains a lactide reactor 2 and a distillation column 3. More particularly, lactide reactor 2 is fed via pipeline 4 with lactic acid oligomers having a polymerization degree approximately between 6 and 50. From these oligomers, crude lactide is manufactured in lactide reactor 2 by means of a ring-closing depolymerization process. This process is catalyzed by means of tin-octoate at appropriate temperature and pressure, all as known in the state of the art. A stream of crude lactide is transported from lactide reactor 2 via pipeline 5 to a distillation column 3.

The crude lactide stream derived from lactide reactor 2 may be in liquid form or in vapor form, depending on the temperature and pressure conditions maintained in lactide reactor 2 and in pipeline 5. In case that the lactide stream is in vapor form, a condenser 6 is positioned in pipeline 3, just behind the lactide reactor 2. In the condenser 6, the lactide and possible other components present in the vapor stream are partly or fully condensed on a cold surface. In case that the lactide stream is in liquid form, no condenser need be present in pipeline 5.

The liquid crude lactide stream is guided via pipeline 5 into distillation column 2. This column 2 has a bottom temperature not higher than 170° C. and a pressure of approximately 50 mbar. Under these conditions, volatile components, like lactic acid, water, lactoyl lactate and a small portion of lactide are removed as low-boiling top-fraction at the top of the column via a pipeline (not shown). A high-boiling bottom fraction is removed under these conditions from distillation column 2 at the bottom of the column via a pipeline (not shown). This fraction comprises compounds like lactic acid oligomers, having a boiling point much higher than the boiling point of lactide.

An intermediate-boiling fraction is removed from distillation column 2 via pipeline 7. Latter fraction comprises lactide in substantially pure form (in excess of 95 wt. %). It is stressed that the lactide present in the pure lactide fraction may be composed of the three stereoisomer L-lactide, meso-lactide and D-lactide. The concentration of these stereoisomers in the pure lactide fraction differ, and is essentially based on the type and optical purity of the lactic acid oligomers and various process conditions applied in the lactide manufacturing process.

An interesting point for measuring the lactide composition, and especially the meso-lactide content as part of the total lactide content of the crude lactide composition is in the crude lactide stream which is derived from the lactide reactor 2 (reference sign 8). In case that a condenser 6 is needed (if the crude lactide is derived as a vapor from the reactor 2), the measuring point can be positioned directly after the condenser. In the absence of a condenser, the measuring point may be positioned in pipeline 5 at any location between the lactide reactor 2 and distillation column 3. Another interesting point for measuring the lactide compositions, and especially the meso-lactide content as part of the total lactide content of the purified lactide composition is in the purified lactide stream which is derived from the distillation column 2 (reference sign 9).

In summary, it has been shown that, with the presently invented meso-lactide quantification method, small amounts of meso-lactide can be determined online by means of IR measurements (both with mid-IR and with near-IR, of which near-IR is preferred) in compositions containing molten L-lactide in a relatively simple manner. This allows direct online monitoring of the production process of lactide.

While the invention has been illustrated and described in detail in the foregoing description, such description is to be considered illustrative or exemplary and not restrictive; the invention is not limited to the disclosed embodiments and experiments. Variations to the disclosed embodiments can be understood and effected by those skilled in the art in practicing the claimed invention, from a study of the disclosure and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The headings used in the specification place no limitation whatsoever on the present invention.

The invention claimed is:

1. Method for quantification of the amount of meso-lactide in a composition containing at least one other lactide stereoisomer with respect to the total amount of lactide stereoisomers in the composition, which method is further comprising absorptions in the Infra-Red region of the electromagnetic spectrum of the composition are determined, and the amount of meso-lactide is quantified with reference to a standard.

2. Method according to claim 1, wherein the amount of meso-lactide is measured at a temperature at which the lactide stereoisomers present in the composition are molten.

3. Method according to claim 1, wherein the amount of meso-lactide is below 25 wt. % of the total amount of lactide stereoisomers present in the composition.

4. Method according to claim 1, wherein the amount of meso-lactide is measured in a lactide production process.

5. Method according to claim 4, wherein the lactide production process is a continuous process.

6. Method according to claim 5, wherein the amount of meso-lactide in the continuous process is measured simultaneously at different stages of the lactide production process.

7. Method according to claim 6, wherein the amount of meso-lactide is measured in a liquid lactide stream which is derived from a condenser onto which lactide has been condensed and subsequently remolten.

8. Method according to claim 6, wherein the amount of meso-lactide is measured in a liquid lactide stream which is derived from the lactide reactor.

9. Method according to claim 5, wherein the results of the quantification of the amounts of meso-lactide with respect of the total amount of lactide enantiomers is used to control production parameters, in order to adjust production of lactide.

10. Method according to claim 4, wherein the measurements are performed continuously during the lactide production process.

11. Method according to claim 4, wherein the lactide is prepared in a lactide reactor by depolymerization of oligomers of lactic acid.

12. Method according to claim 11, wherein lactide removed from the lactide reactor is subsequently purified.

13. Method according to claim 12, wherein the lactide removed from the lactide reactor is purified by means of a distillation column, and the amount of meso-lactide is measured in a liquid lactide stream which is derived from the distillation column.

14. Method according to claim 1, wherein the quantification is based on measurements performed on absorptions in only the near Infra-Red region of the electromagnetic spectrum.

* * * * *